(12) United States Patent
Ge et al.

(10) Patent No.: US 9,803,565 B1
(45) Date of Patent: Oct. 31, 2017

(54) SYSTEM AND METHOD FOR MEASURING QUALITY OF FUEL

(71) Applicant: Caterpillar Inc., Peoria, IL (US)

(72) Inventors: Xinyu Ge, Peoria, IL (US); James Cairns, Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 15/162,652

(22) Filed: May 24, 2016

(51) Int. Cl.
| | |
|---|---|
| F02M 65/00 | (2006.01) |
| F02D 19/08 | (2006.01) |
| G01N 25/18 | (2006.01) |
| G01N 33/28 | (2006.01) |
| F02D 41/00 | (2006.01) |

(52) U.S. Cl.
CPC ....... F02D 19/087 (2013.01); F02D 41/0025 (2013.01); F02M 65/00 (2013.01); G01N 25/18 (2013.01); G01N 33/2829 (2013.01); F02D 2200/0611 (2013.01)

(58) Field of Classification Search
CPC .. F02D 19/087; F02D 19/085; F02D 41/0025; F02D 41/0045; F02M 41/0045; G01N 33/2829
See application file for complete search history.

(56) References Cited

U.S. PATENT DOCUMENTS

| 5,791,145 A | 8/1998 | Freen |
| 7,210,455 B2 | 5/2007 | Visser et al. |
| 2015/0090222 A1 | 4/2015 | Rebinsky |
| 2015/0114357 A1* | 4/2015 | Fujino ............... F02D 41/20 123/490 |
| 2015/0300273 A1 | 10/2015 | Hunter |

FOREIGN PATENT DOCUMENTS

EP      1279534      8/2004

* cited by examiner

*Primary Examiner* — Kevin A Lathers

(57) ABSTRACT

A system for measuring quality of fuel in an engine is disclosed. The system includes a fuel quality measuring unit and a controller in communication with the fuel quality measuring unit. The fuel quality measuring unit includes a first valve, a second valve, and a quality measurement sensor disposed between the first valve and the second valve. The controller is configured to determine whether the engine is running in a steady state condition, and identify a measurement window based on a pressure of the fuel at an inlet, an Intake Manifold Pressure (IMP), and the steady state condition. The controller is configured to control an opening and a closing of the first valve, the second valve, and a fuel metering valve during the measurement window. The controller is configured to determine the quality of the fuel captured between the first valve and the second valve by the quality measurement sensor.

20 Claims, 6 Drawing Sheets

SYSTEM AND METHOD FOR MEASURING QUALITY OF FUEL

TECHNICAL FIELD

The present disclosure relates to measuring quality of fuel in an engine, and more particularly to a system and a method to measure quality of fuel in an engine.

BACKGROUND

An air-fuel ratio is a critical parameter for operating an engine, and may vary based on power requirements. It is relevant to ensure a suitable air-fuel ratio for an effective operation of the engine at all times. Any undesirable change in the air-fuel ratio may hamper operations of the engine and may even lead to damage to the engine. In order to monitor the air-fuel ratio, quality measurement sensors are disposed in the engine. In some cases, a quality measurement sensor is installed in an exhaust system of the engine. In such cases, undesired emission, due to the combustion of an air-fuel mixture, may have already occurred by the time the quality measurement sensor detects inappropriate air-fuel ratio. Alternatively, the quality measurement sensor may be installed in a fuel supply system of the engine, with one or two shut-off valves and a conduit for measuring quality of the fuel. Installation, operation, and maintenance of such shut-off valves and the conduit is a cumbersome and expensive task. This would lead to economical loss, unnecessary downtime, inconvenience, and ineffective operations of the engine.

U.S. Pat. No. 7,210,455 (the '455 patent) discloses a system that uses a fuel quality sensor to control various aspects of engine operation. In this regard, an acoustic wave sensor is used to measure viscosity and density of gasoline fuels. The measured viscosity and density, of gasoline fuels, are to predict engine combustion quality during an engine start. Based on the prediction, engine operating parameters (such as fuel injection amount and ignition timing) are adjusted for achieving improved vehicle driveability and engine combustion. However, the system of the '455 patent offers a fragmented and a relatively inaccurate approach for measuring the quality of the fuel in a fuel tank of the engine.

SUMMARY OF THE DISCLOSURE

In one aspect of the present disclosure, a system for measuring quality of fuel in an engine is provided. The system includes a fuel quality measuring unit disposed between a fuel admission valve and an intake manifold of the engine. The fuel quality measuring unit includes a first valve fluidly coupled to the fuel admission valve, a second valve fluidly coupled to the intake manifold, and a quality measurement sensor disposed between the first valve and the second valve. The system further includes a controller in communication with the fuel quality measuring unit. The controller is configured to determine whether the engine is running in a steady state condition based on one or more engine operating parameters. The controller is further configured to identify a measurement window based on a pressure of the fuel at an inlet to the fuel quality measuring unit, an Intake Manifold Pressure (IMP), and determining whether the engine is running in the steady state condition. The measurement window is indicative of a time duration when a value of at least one calibration parameter of the engine is within a predefined range of calibration points for the at least one calibration parameter. The controller is configured to control an opening and a closing of the first valve, the second valve, and a fuel metering valve of the engine during the measurement window, based on a predefined control map. The opening and the closing are controlled for capturing the fuel between the first valve and the second valve. The controller is configured to determine the quality of the fuel captured between the first valve and the second valve based on one or more values detected by the quality measurement sensor.

In another aspect of the present disclosure, a method for determining quality of fuel in an engine is provided. The method includes determining, by a controller, whether the engine is running in a steady state condition based on one or more engine operating parameters. The method includes identifying, by the controller, a measurement window based on a pressure of the fuel at an inlet to a fuel quality measuring unit disposed between a fuel admission valve and an intake manifold of the engine, an Intake Manifold Pressure (IMP), and the determination of whether the engine is running in the steady state condition. The measurement window is indicative of a time duration when a value of at least one calibration parameter is within a predefined range of calibration points for the at least one calibration parameter. The method further includes controlling, by the controller, an opening and a closing of a first valve, a second valve, and a fuel metering valve of the engine during the measurement window, based on a predefined control map. The opening and the closing are controlled for capturing the fuel between the first valve and the second valve. The first valve is fluidly coupled to the fuel admission valve, and the second valve is fluidly coupled to the intake manifold. The method includes determining, by the controller, the quality of fuel captured between the first valve and the second valve based on one or more values detected by a quality measurement sensor of the fuel quality measuring unit disposed between the first valve and the second valve.

In yet another aspect of the present disclosure, a system for measuring quality of fuel in an engine is provided. The system includes a fuel quality measuring unit disposed between a fuel admission valve and an intake manifold of the engine. The fuel quality measuring unit includes a first valve fluidly coupled to the fuel admission valve, a second valve fluidly coupled to the intake manifold, and a quality measurement sensor disposed between the first valve and the second valve. The fuel quality measuring unit includes a controller in communication with the fuel quality measuring unit. The controller is configured to receive an input being indicative of an attempt to quick-start the engine. The controller is configured to open the first valve and the second valve for receiving the fuel from the fuel admission valve based on the input for quick-starting of the engine. The controller is further configured to close the first valve and the second valve, once the engine is quick-started, for capturing the fuel between the first valve and the second valve. The controller is configured to determine the quality of the fuel captured between the first valve and the second valve based on one or more values detected by the quality measurement sensor.

Other features and aspects of this disclosure will be apparent from the following description and the accompanying drawings.

DETAILED DESCRIPTION

Figure 1:
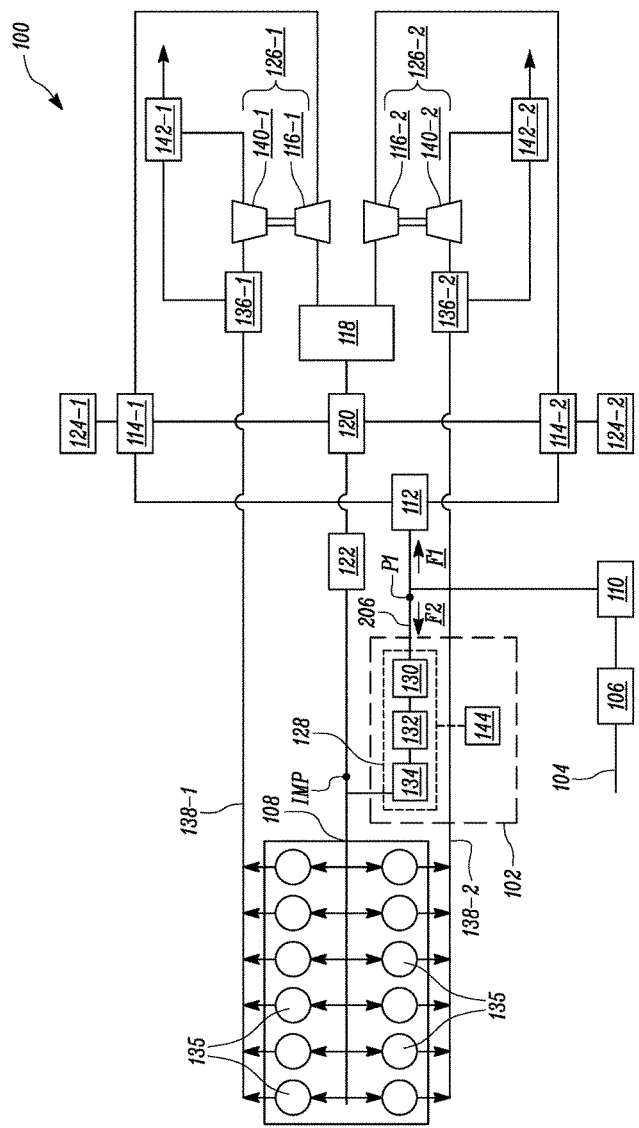
FIG. 1 is a schematic view of an engine with a system for measuring quality of fuel in the engine, according to one implementation of the present disclosure.

Wherever possible, the same reference numbers will be used throughout the drawings to refer to the same or the like parts. FIG. 1 illustrates a schematic view of an engine 100 with a system 102 for measuring quality of fuel in the engine 100, according to one implementation of the present disclosure. The engine 100 may be a gas engine running on one of natural gas, coal gas, mine gas, biogas, landfill gas, or sewage gas.

The fuel is introduced into the engine 100 through a fuel supply conduit 104. The engine 100 may include a fuel regulator 106 receiving the fuel through the fuel supply conduit 104. The fuel regulator 106 may regulate a pressure of the fuel before the fuel approaches an intake manifold 108 of the engine 100. The fuel regulator 106 may regulate the pressure of the fuel based on various factors, such as a load of the engine 100, power requirements of the engine 100, a type of the engine 100, and an operating condition of the engine 100.

Once the fuel regulator 106 regulates the pressure of the fuel, the fuel may be delivered to a fuel admission valve 110. The fuel admission valve 110 may be understood as a shut-off valve for allowing or blocking a passage of the fuel towards the intake manifold 108. For example, when the fuel admission valve 110 is in an open state, the fuel may be allowed to move towards the intake manifold 108. On the other hand, when the fuel admission valve 110 is in a closed state, the passage of the fuel towards the intake manifold 108 may be blocked.

Once the fuel may be allowed to pass through the fuel admission valve 110, the fuel may approach towards the intake manifold 108 through one of a first flow path "F1" or a second flow path "F2". In some implementations, the fuel may follow the first flow path "F1" for starting the engine 100 as well as for running the engine 100 thereafter. In some implementations, the fuel may follow the second flow path "F2" for quick-starting the engine 100. Since the second flow path "F2" is shorter as compared to the first flow path "F1", the engine 100 may take lesser time for starting, which is referred to as the quick-starting of the engine 100. Once the engine 100 is quick-started, the fuel may switch to the first flow path "F1" for running the engine 100 thereafter.

The first flow path "F1" may include a fuel metering valve 112, at least one mixer apparatus 114, at least one compressor unit 116, a charge air cooler 118, a compressor bypass valve 120, and a throttle valve 122 disposed upstream with respect to the intake manifold 108. The fuel flowing from the fuel admission valve 110 may be introduced into the first flow path "F1" through the fuel metering valve 112. The fuel metering valve 112 may be disposed to control a fuel flow or a mass flow rate of the fuel moving towards the at least one mixer apparatus 114. The fuel metering valve 112 may be understood as a proportional valve which may be variably controlled to allow a variable flow rate of the fuel through the first flow path "F1".

From the fuel metering valve 112, the fuel may be delivered to the at least one mixer apparatus 114. In some implementations, the at least one mixer apparatus 114 may include a pair of mixer apparatuses 114, which may be individually referred to as 114-1 and 114-2. The at least one mixer apparatus 114 may be configured to form an air-fuel mixture, to be fed to the intake manifold 108, by mixing the fuel received from the fuel metering valve 112 with air. In some implementations, the at least one mixer apparatus 114 may receive air from one or more air storage compartments 124. In some implementations, the one or more air storage compartments 124 may filter the air before introducing the air into the at least one mixer apparatus 114. In the present implementation, since there is the pair of mixer apparatuses 114, the engine 100 may include a pair of air storage compartments 124, individually referred to as 124-1 and 124-2. The at least one mixer apparatus 114 may form the air-fuel mixture based on a predetermined air-fuel ratio. The at least one mixer apparatus 114 may form a rich air-fuel mixture or a lean air-fuel mixture based on the predetermined air-fuel ratio. In some implementations, the at least one mixer apparatus 114 may be a carburetor.

Following the formation of the air-fuel mixture by the at least one mixer apparatus 114, the air-fuel mixture may be delivered to the at least one compressor unit 116. In the present implementation, the engine 100 may include a pair of compressor units 116, individually referred to as 116-1 and 116-2. Each of the pair of compressor units 116-1 and 116-2 may be disposed downstream with respect to the pair of mixer apparatuses 114-1 and 114-2, respectively. The at least one compressor unit 116 may compress the air-fuel mixture. In some implementations, the at least one compressor unit 116 may be a component of at least one turbocharger 126. The engine 100 may include a pair of turbochargers 126, individually referred to as turbocharger 126-1 and turbocharger 126-2. The air-fuel mixture compressed by the at least one compressor unit 116 may then be delivered to the charge air cooler 118.

The charge air cooler 118 may be disposed to decrease temperature of the air-fuel mixture. As a result, a high-density low-temperature air-fuel mixture may be obtained as an output of the charge air cooler 118. From the charge air cooler 118, the air-fuel mixture may be delivered to the compressor bypass valve 120.

In some implementations, an amount of the air-fuel mixture, which is to be delivered to the intake manifold 108, may be less than an amount of the air-fuel mixture delivered from the charge air cooler 118. The compressor bypass valve 120 may divert a surplus amount of the air-fuel mixture back to the at least one mixer apparatus 114. The surplus amount of the air-fuel mixture may then be forwarded to the at least one compressor unit 116 for a next delivery of the air-fuel mixture to the intake manifold 108. Therefore, the compressor bypass valve 120 may deliver a desired amount of the air-fuel mixture to the throttle valve 122, by diverting the surplus amount back to the at least one compressor unit 116.

The throttle valve 122 may control a flow rate of the air-fuel mixture received from the compressor bypass valve 120 entering the intake manifold 108. In some implementations, the throttle valve 122 may control the flow rate based on an engine operating condition. For example, in an idle operating condition of the engine 100, the throttle valve 122 may decrease the flow rate of the air-fuel mixture entering the intake manifold 108, which decreased flow rate may be less than a flow rate of the air-fuel during a full-load operating condition of the engine 10.

In some implementations, the fuel from the fuel admission valve 110 may follow the second flow path "F2" for reaching the intake manifold 108. The second flow path "F2" may include a fuel quality measuring unit 128. The fuel quality measuring unit 128 may include a first valve 130 coupled to the fuel admission valve 110, a quality measurement sensor 132 coupled to the first valve 130, and a second valve 134 coupled to the intake manifold 108. The first valve 130 and the second valve 134 may be configured to allow the fuel to bypass the first flow path "F1", for quick-starting the engine 100. In some implementations, the first valve 130 and the second valve 134 may be proportional valves. A proportional valve is a valve which may allow for a change in an output value in proportion to a change in an inlet value. For example, an amount of the fuel exiting the first valve 130 or the second value 134 is in proportion to an amount of the fuel entering first valve 130 or the second valve 134, respectively.

When in an open state, the first valve 130 may allow a passage of the fuel from the fuel admission valve 110 to the intake manifold 108 through the fuel quality measuring unit 128. The fuel from the first valve 130 may be delivered to the second valve 134 through the quality measurement sensor 132. The quality measurement sensor 132, which is disposed downstream with respect to the first valve 130, may detect one or more values pertaining to the quality of the fuel. Further, when in an open state, the second valve 134, which is disposed downstream with respect to the quality measurement sensor 132, may control a fuel flow rate and may allow the fuel to reach the intake manifold 108.

In order to precisely detect the one or more values by the quality measurement sensor 132, the fuel around the quality measurement sensor 132 has to be in a stationary flow condition. The stationary flow condition of the fuel may be understood as a condition in which the fuel is stationary and not flowing around the quality measurement sensor 132. For achieving the stationary flow condition of the fuel, the first valve 130 and the second valve 134 may be opened and closed for capturing the fuel between the first valve 130 and the second valve 134. The quality measurement sensor 132 may then detect the one or more values pertaining to the quality of the fuel.

When the air-fuel mixture reaches the intake manifold 108, through one of the first flow path "F1" or the second flow path "F2", the air-fuel mixture may be combusted in combustion chambers (not shown) defined in a plurality of cylinders 135 of the engine 100. After combustion, exhaust gases from the intake manifold 108 may be delivered to at least one waste-gate valve 136 through exhaust conduits 138, individually referred to as 138-1 and 138-2. In some implementations, the engine 100 may include a pair of waste-gate valves 136, individually referred to as waste-gate valve 136-1 and waste-gate valve 136-2 which may be disposed in the exhaust conduit 138-1 and the exhaust conduit 138-2, respectively. In some implementations, the at least one waste-gate valve 136 may be incorporated within the at least one turbocharger 126.

In some implementations, the at least one waste-gate valve 136 may be biased towards a close position by default. In some implementations, when a flow rate of the exhaust gases is below a predefined threshold value for opening the at least waste-gate valve 136, the exhaust gases may flow through at least one turbine unit 140 of the engine 100. The exhaust gases may expand against vanes of the turbine unit 140 (not shown) thereof to rotate the at least one turbine unit 140. In the illustrated implementation, the engine 100 may include a pair of turbine units 140, individually referred to as turbine unit 140-1 and turbine unit 140-2. In some implementations, the turbine unit 140-1 and the turbine unit 140-2 may be of the turbocharger 126-1 and the turbocharger 126-2, respectively. Continuing with the present implementation, after rotating the at least one turbine unit 140, the exhaust gases may flow to after-treatment systems 142, individually referred to as after-treatment system 142-1 and after-treatment system 142-2 corresponding to the turbine unit 140-1 and turbine unit 140-2, respectively. The after-treatment systems 142 may treat the exhaust gases for harmful emissions before releasing the exhaust gases into the atmosphere.

In some implementations, when the flow rate of the exhaust gases is equal to or above the predefined threshold value for opening the at least one waste-gate valve 136, the at least one waste-gate valve 136 may allow the exhaust gases to bypass the at least one turbine unit 140 and move directly towards the after-treatment systems 142.

In some implementations, the engine 100 may be running in one of a plurality of operational modes. The plurality of operational modes may include, but is not limited to, a quick-start mode and/or a normal operation mode. The quick-start mode of the engine 100 may be understood as an operational mode in which the engine 100 is being quick-started, and the fuel may be flowing through the second flow path "F2" to reach the intake manifold 108, as explained previously. The normal operation mode may be understood as an operational mode of the engine 100 in which the engine 100 is started, and the fuel may be flowing through the first flow path "F1" to reach the intake manifold 108.

The engine 100 may include the system 102 for determining the quality of the fuel in the quick-start mode as well as the normal operation mode. In some implementations, the system 102 may include the fuel quality measuring unit 128 and a controller 144 in communication with the fuel quality measuring unit 128. The controller 144 may determine the quality of the fuel captured between the first valve 130 and the second valve 134. The constructional and operational details of the system 102 are explained in detail in the description of FIG. 2.

Figure 2:
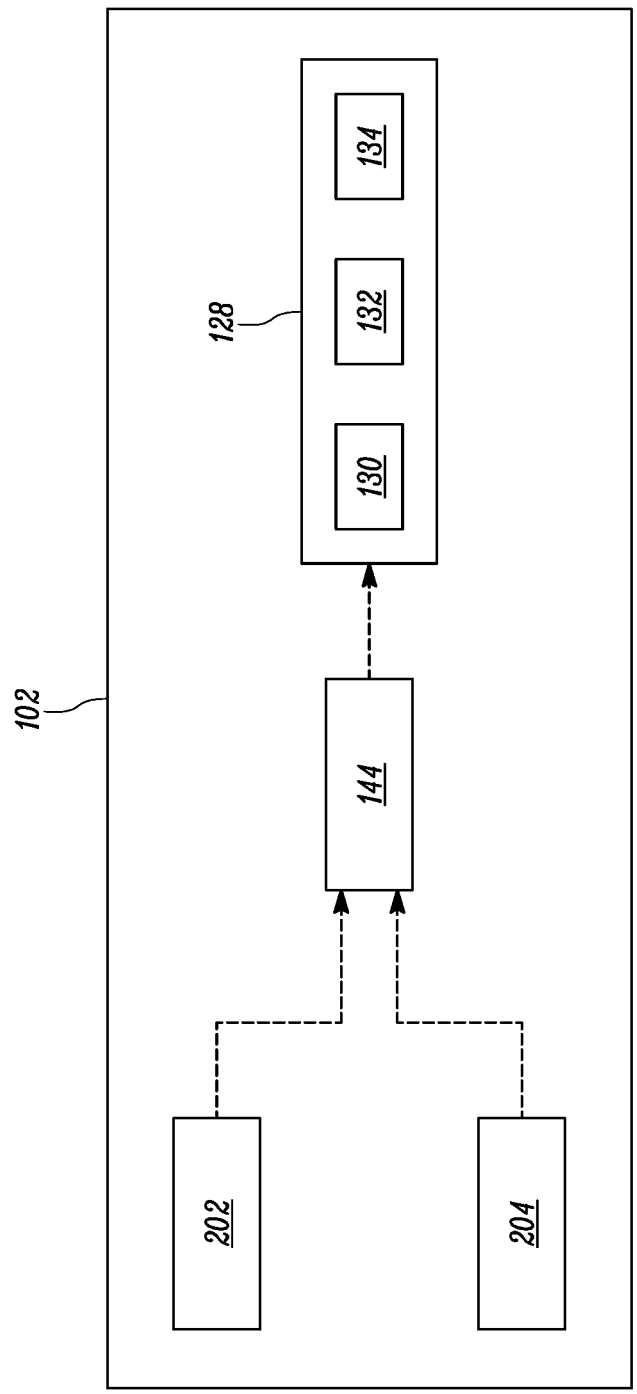
FIG. 2 is a block diagram of the system, according to one implementation of the present disclosure.

FIG. 2 illustrates a block diagram of the system 102, according to one implementation of the present disclosure. The system 102 may include a first set of sensors 202, a second set of sensors 204, the controller 144, and the fuel quality measuring unit 128. The first set of sensors 202, the second set of sensors 204, and the fuel quality measuring unit 128 may be in an operable communication with the controller 144. In some implementations, the first set of sensors 202 may be configured to detect an Intake Manifold Pressure (IMP) (shown in FIG. 1) and a pressure "P1" (shown in FIG. 1) of the fuel at an inlet 206 (shown in FIG. 1) to the fuel quality measuring unit 128. The "IMP" may be defined as a pressure of the air-fuel mixture passing through the intake manifold 108.

In some implementations, the second set of sensors 204 may be configured to detect at least one value of one or more engine operating parameters. The one or more engine operating parameters may be understood as parameters or factors which may affect an overall operation of the engine 100. In some implementations, the one or more engine operating parameters may include, but are not limited to, an engine speed, an engine load, a coolant temperature, a compressor out-pressure, a waste-gate valve position, a throttle valve position, and/or a compressor bypass valve position.

Figure 3:
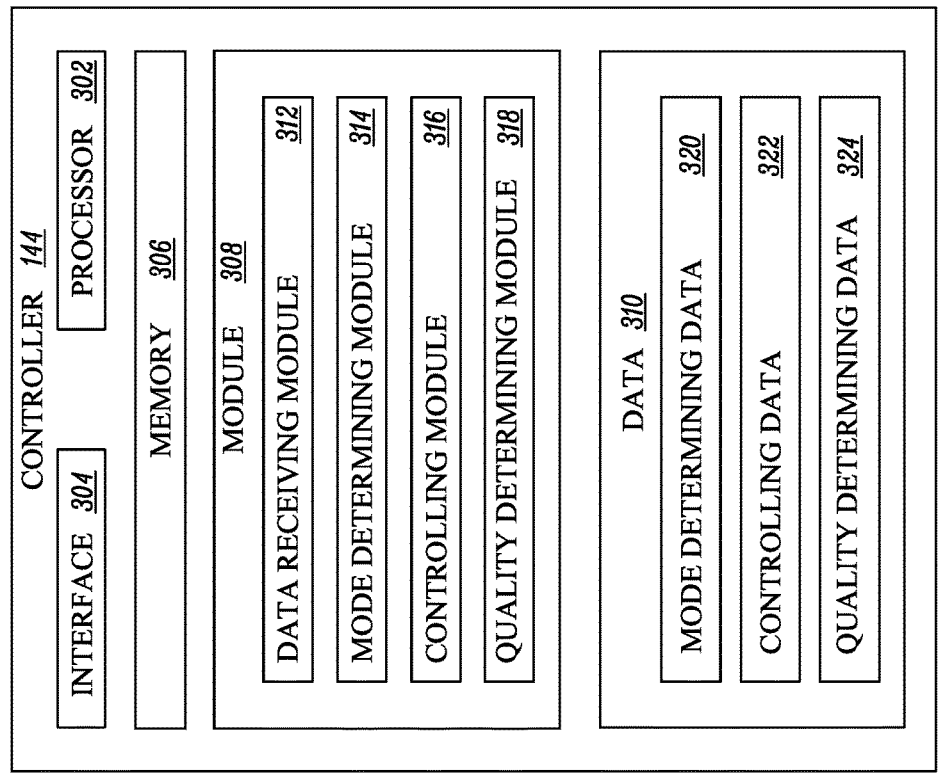
FIG. 3 is a block diagram of a controller of the system, according to one implementation of the present disclosure.

The data as detected by the first set of sensors 202 and the second set of sensors 204 may be forwarded to the controller 144. The constructional and operational details of the controller 144 can be understood by referring to FIG. 2 in conjunction with FIG. 3. FIG. 3 illustrates a block diagram of the controller 144 of the system 102, according to one implementation of the present disclosure.

Referring to FIG. 2 and FIG. 3, the controller 144 may include a processor 302, an interface 304, and a memory 306 coupled to the processor 302. The processor 302 may be configured to fetch and execute computer readable instructions stored in the memory 306. In some implementations, the processor 302 may be implemented as one or more microprocessors, microcomputers, microcontrollers, digital signal processors, central processing units, state machine, logic circuitries or any devices that manipulate signals based on operational instructions.

The interface 304 may facilitate multiple communications within wide variety of protocols and networks, including wired network. Further, the interface 304 may include a variety of software and hardware interfaces. In some implementations, the interface 304 may include, but is not limited to, peripheral devices, such as a keyboard, a mouse, an external memory, and/or a printer. The interface 304 may facilitate multiple communications within wide variety of protocols and networks, including wired network. In one example, the interface 304 may include one or more ports for connecting the controller 144 to an output unit (not shown).

In some implementations, the memory 306 may include any non-transitory computer-readable medium. In one example, the non-transitory computer-readable medium may be a volatile memory, such as static random access memory and a non-volatile memory, such as read-only memory, erasable programmable ROM, and flash memory.

The controller 144 may include modules 308 and data 310. The modules 308 may include hardware and/or software (routines, programs, objects, components, and data structures) which perform particular tasks or implement particular data types. In some implementations, the modules 308 may include a data receiving module 312, a mode determining module 314, a controlling module 316, and a quality determining module 318. The data 310 may be included in a repository for storing data processed, received, and generated by one or more of the modules 308. The data 310 may include a mode determining data 320, a controlling data 322, and a quality determining data 324.

In some implementations, the engine 100 may be running in the normal operation mode. The data receiving module 312 may receive the data as detected by the first set of sensors 202 and the second set of sensors 204. In the present implementation, the data receiving module 312 may receive the "IMP", and the pressure "P1" of the fuel at the inlet 206 to the fuel quality measuring unit 128 from the first set of sensors 202. Further, the data receiving module 312 may receive the at least one value of the one or more engine operating parameters from the second set of sensors 204.

Based on the one or more engine operating parameters, the mode determining module 314 may determine whether the engine 100 is running in a steady state condition. In some implementations, the mode determining module 314 may determine whether the engine 100 is running in the steady state condition based on the at least one value of the one or more engine operating parameters received from the second set of sensors 204.

The steady state condition of the engine 100 may be understood as an operating condition when the at least one value of the one or more engine operating parameters is constant over a predetermined time duration. For example, if the predetermined time duration is 3 minutes, the engine 100 is in the steady state condition when the at least one value of the one or more engine operating parameters is found to be substantially constant for at least 3 minutes. In some implementations, the steady state condition of the engine 100 may be indicative of the at least one value being in a predefined range for the predetermined time duration. In some implementations, the predefined range of the at least value for each of the one or more engine operating parameters may be stored in an Engine Control Module (ECM) (not shown). In some implementations, details pertaining to the mode determining module 314 may be stored in the mode determining data 320.

Once the engine 100 is found to be in the steady state condition by the mode determining module 314, the controlling module 316 may identify a measurement window based on at least one calibration parameter, the pressure "P1", and the "IMP". The measurement window is indicative of a time duration when a value of the at least one calibration parameter is within a predefined range of calibration points for the at least one calibration parameter. The at least one calibration parameter may correspond to engine performance characteristics. In some implementations, the at least one calibration parameter may include, but is not limited to, an ignition mode, an ignition timing, and/or a fuel quantity.

The controlling module 316 may identify an occurrence of the measurement window, when the value of the at least one calibration parameter may fall within the predefined range of calibration points, for example, +/−3% within a predefined set value. In some implementations, the controlling module 316 may identify the occurrence of the measurement window, when the value of the at least one calibration parameter is substantially equal to a corresponding predefined set value.

In some implementations, the controlling module 316 may refer to engine calibration maps or reference tables to obtain the predefined range of calibration points corresponding to the at least one calibration parameter. The engine calibration maps or reference tables may be set during an engine calibration process and stored in the ECM of the engine 100. In some implementations, the predefined range of calibration points, corresponding to the at least one calibration parameter, may be defined for various operating conditions of the engine 100.

For example, when the engine 100 is running at 1800 rpm, the controlling module 316 may monitor the at least one calibration parameter. When the value of the at least one calibration parameter is found to be within the corresponding predefined range of calibration points, the controlling module 316 may identify the occurrence of the measurement window for such operating conditions. During the measurement window, the pressure "P1" may be greater than the "IMP".

Upon identifying the measurement window, the controlling module 316 may control an opening and a closing of the first valve 130, of the fuel quality measuring unit 128, and an opening and a closing of the second valve 134, of the fuel quality measuring unit 128, during the measurement window. The controlling module 316 may control the opening and the closing of the first valve 130 and the second valve 134 for capturing the fuel between the first valve 130 and the second valve 134. When the pressure "P1" is greater than the "IMP" during the measurement window, the fuel between the throttle valve 122 and the intake manifold 108 may not back flow through the second valve 134 and the first valve 130, when the first valve 130 and the second valve 134 are in the open state. Further, the controlling module 316 may also control the fuel metering valve 112 and the second valve 134, of the engine 100, in order to maintain a desired air-fuel ratio and a desired amount of the air-fuel mixture entering the intake manifold 108, according to the engine calibration maps.

The controlling module 316 may control the first valve 130 and the second valve 134 based on a predefined control map. The controlling module 316 may obtain the predefined control map from the ECM. In some implementations, the predefined control map may include details pertaining to the opening and/or the closing of the first valve 130, the second valve 134, and/or the fuel metering valve 112. The details may include, but are not limited to, a sequence and a time duration of the opening and/or the closing of the first valve 130, the second valve 134, and/or the fuel metering valve 112. The predefined control map may include such details specific to various values of each of the one or more engine operating parameters, the at least one calibration parameter, and the operating conditions of the engine 100 recorded during engine operation. For example, for each value of the engine load recorded during the engine operation, the controlling module 316 may control the first valve 130, the second valve 134, and/or the fuel metering valve 112 based on the details corresponding to the recorded value of the engine load available in the predefined control map.

Once the fuel is captured between the first valve 130 and the second valve 134, the quality determining module 318 may determine the quality of the captured fuel. For example, the quality determining module 318 may determine the quality of the fuel, when the fuel is in the stationary flow condition. The quality determining module 318 may determine the quality of the fuel based on the one or more values detected by the quality measurement sensor 132. In some implementations, the quality determining module 318 may determine the quality of the fuel based on characteristics of heat transfer within the fuel and a thermal conductivity of the fuel. Therefore, the one or more values, detected by the quality measurement sensor 132, are derived by the quality measurement sensor 132, according to empirical data.

In some implementations, the quality determining module 318 may determine the heat transfer and the thermal conductivity based on a Fourier heat transfer equation. For example, the quality determining module 318 may determine the heat transfer within the fuel based on the Fourier heat transfer equation. Further, the quality determining module 318 may determine the thermal conductivity based on the heat transfer. The thermal conductivity may then be utilized to determine the quality of the fuel.

In one example, for determining the quality of the fuel, the quality determining module 318 may compare the one or more values with a range of values predefined for a plurality of quality zones. For example, the plurality of quality zones may include, but are not limited to, excellent, good, average, and/or poor with corresponding range of values as "A-B", "B-C", "C-D", and/or "D-E", respectively. Therefore, the quality determining module 318 may determine a range of values the one or more values would fall in, and accordingly, the quality of the fuel may be determined as excellent, good, average, and/or bad.

In an alternate implementation, the engine 100 may be running in the quick-start mode. In such an implementation, the data receiving module 312 may receive an input indicative of an attempt to quick-start the engine 100. In some implementations, an input device (not shown), such as a lever and a push-button may be disposed in a control panel (not shown) of the engine 100. When an operator uses the input device, the data receiving module 312 may receive the input indicative of an instruction for quick-starting the engine 100. In some implementations, details pertaining to the data receiving module 312 may be stored in the mode determining data 320.

Based on the input received by the data receiving module 312, the controlling module 316 may open the first valve 130 and the second valve 134 for receiving the fuel from the fuel admission valve 110. Since the first valve 130 and the second valve 134 are in the open state, the fuel may flow through the second flow path "F2" for reaching the intake manifold 108 from the fuel admission valve 110.

Once the engine 100 is quick-started, the controlling module 316 may close the first valve 130 and the second valve 134. In some implementations, the starting of the engine 100 may be detected based on the at least one value of the one or more engine operating parameters as detected by the second set of sensors 204. For example, the starting of the engine 100 may be detected when the temperature, of a coolant in the engine 100, exceeds a threshold temperature (e.g., 80 degree Celcius (° C.)). The opening and/or the closing of the first valve 130 and the second valve 134 may result into capturing of the fuel between the first valve 130 and the second valve 134. In some implementations, details pertaining to the controlling module 316 may be stored in the controlling data 322.

In continuation with capturing of the fuel, the quality determining module 318 may determine the quality of the fuel captured between the first valve 130 and the second valve 134, based on the one or more values detected by the quality measurement sensor 132, when the engine 100 is running in the normal operation mode.

In some implementations, following the determination of the quality of the fuel, the quality determining module 318 may generate a report indicative of the quality of the fuel. In one example, the report may include a value indicating the quality of the fuel for determining whether the fuel is suitable to be used in the engine 100. The report may also include a brief description of a plurality of quality zones with corresponding range of values for rating the quality of the fuel. The determined value of the fuel may be compared against the range of values of the plurality of quality zones to analyze the quality of the fuel. The quality determining module 318 may provide the report to the ECM or the operator through an output unit (not shown). In some implementations, details pertaining to the quality determining module 318 may be stored in the quality determining data 324.

INDUSTRIAL APPLICABILITY

The present disclosure relates to the system 102 and methods 400, 500, 600 for measuring the quality of the fuel in the engine 100. The system 102 may include the fuel quality measuring unit 128 and the controller 144 in communication with the fuel quality measuring unit 128. The fuel quality measuring unit 128 may include the first valve 130, the quality measurement sensor 132, and the second valve 134. The first valve 130, the quality measurement sensor 132, and the second valve 134 may be in fluid communication with each other. The first valve 130 and the second valve 134 may already be disposed in the engine 100 for quick-starting the engine 100. Therefore, for implementing the system 102 in the engine 100, the quality measurement sensor 132 may be disposed between the first valve 130 and the second valve 134.

The controller 144 may control the opening and the closing of the first valve 130 and the second valve 134 for capturing the fuel between the first valve 130 and the second valve 134. The quality measurement sensor 132 then detects one or more values pertaining to the quality of the fuel, when the fuel is in the stationary flow condition. The controller 144 may also control the fuel metering valve 112 in conjunction with the first valve 130 and the second valve 134 to ensure that the desired amount of the air-fuel mixture is fed to the intake manifold 108. In some implementations, the controller 144 may be provided on-board the engine 100. In some implementations, the controller 144 may be provided off-board the engine 100. The system 102 may determine the quality of the fuel by controlling the first valve 130, the second valve 134, and the fuel metering valve 112, in the quick-start mode as well as the normal operation mode of the engine 100.

Figure 4:
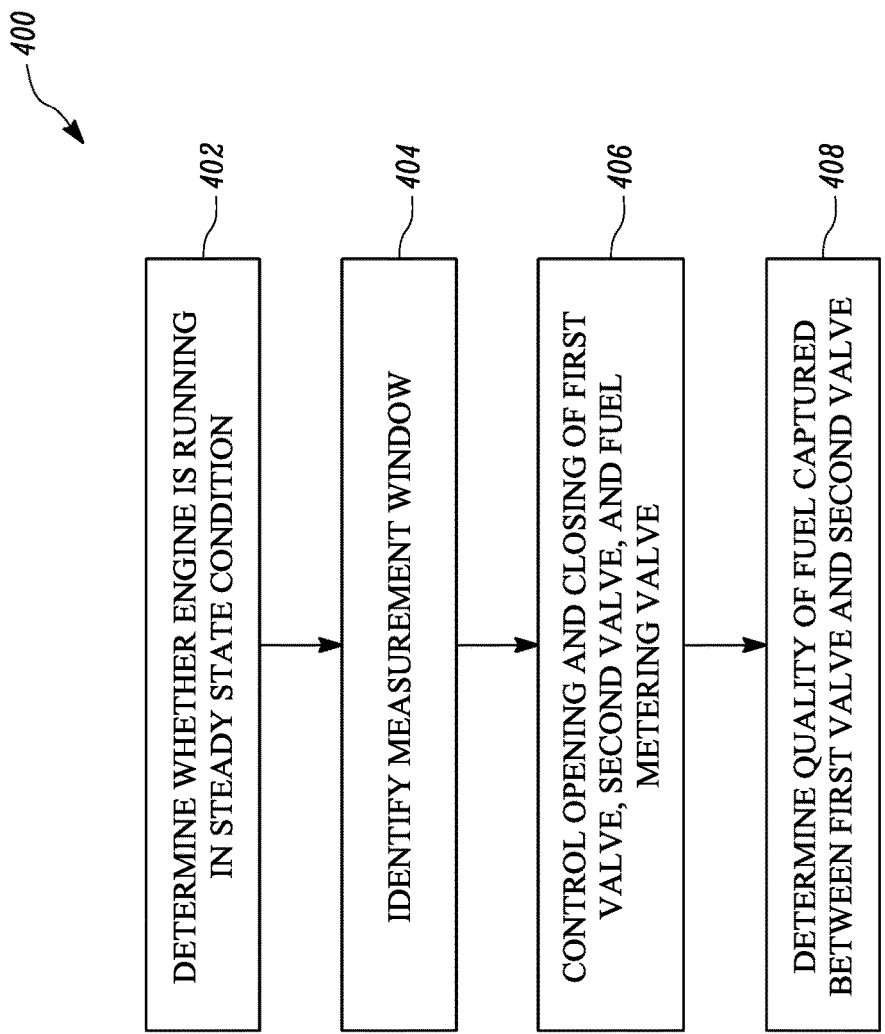
FIG. 4 is a flowchart for a method for determining quality of fuel in the engine, according to one implementation of the present disclosure.

FIG. 4 illustrates a flowchart for the method 400 for determining the quality of the fuel in the engine 100, according to one implementation of the present disclosure. The method 400 is for determining the quality of the fuel, when the engine 100 is in the normal operation mode. For the sake of brevity, some aspects of the present disclosure which are already explained in detail in the description of FIG. 1, FIG. 2, and FIG. 3 are not explained in the description of FIG. 4.

At block 402, the method 400 may include determining whether the engine 100 is running in the steady state condition. The steady state condition of the engine 100 may be determined based on the one or more engine operating parameters. In some implementations, the steady state condition of the engine 100 may be determined based on the at least one value of the one or more engine operating parameters. The engine 100 may be in the steady state condition when the at least one value, of the one or more engine operating parameters, is constant over the predetermined time duration. In some implementations, the mode determining module 314 of the controller 144 of the system 102 may determine whether the engine 100 is running in the steady state condition.

At block 404, the method 400 may include identifying the measurement window. During the measurement window, the pressure "P1" of the fuel at the inlet 206 to the fuel quality measuring unit 128 may be greater than the "IMP". The fuel quality measuring unit 128 may be disposed between the fuel admission valve 110 and the intake manifold 108 of the engine 100. The measurement window may be indicative of the time duration when the value of the at least one calibration parameter is within the predefined range of calibration points corresponding to the at least one calibration parameter. In some implementations, the controlling module 316 of the controller 144 may identify the measurement window.

At block 406, the method 400 may include controlling the opening and the closing of the first valve 130, the second valve 134, and the fuel metering valve 112 during the measurement window, based on the predefined control map. The first valve 130 and the second valve 134 may be controlled to capture the fuel between the first valve 130 and the second valve 134. The first valve 130 and the second valve 134 may be controlled to create the stationary flow condition of the fuel between the first valve 130 and the second valve 134. The first valve 130 may be fluidly coupled to the fuel admission valve 110 and the second valve 134 may be fluidly coupled to the intake manifold 108. In some implementations, the controlling module 316 of the controller 144 may control the first valve 130, the second valve 134, and the fuel metering valve 112.

At block 408, the method 400 may include determining the quality of the fuel captured between the first valve 130 and the second valve 134. The quality may be determined based on the one or more values as detected by the quality measurement sensor 132 disposed between the first valve 130 and the second valve 134. In some implementations, the quality of the fuel may be determined based on at least one of the heat transfer within the fuel or the thermal conductivity of the fuel. In some implementations, the quality determining module 318 of the controller 144 may determine the quality of the fuel.

Figure 5:
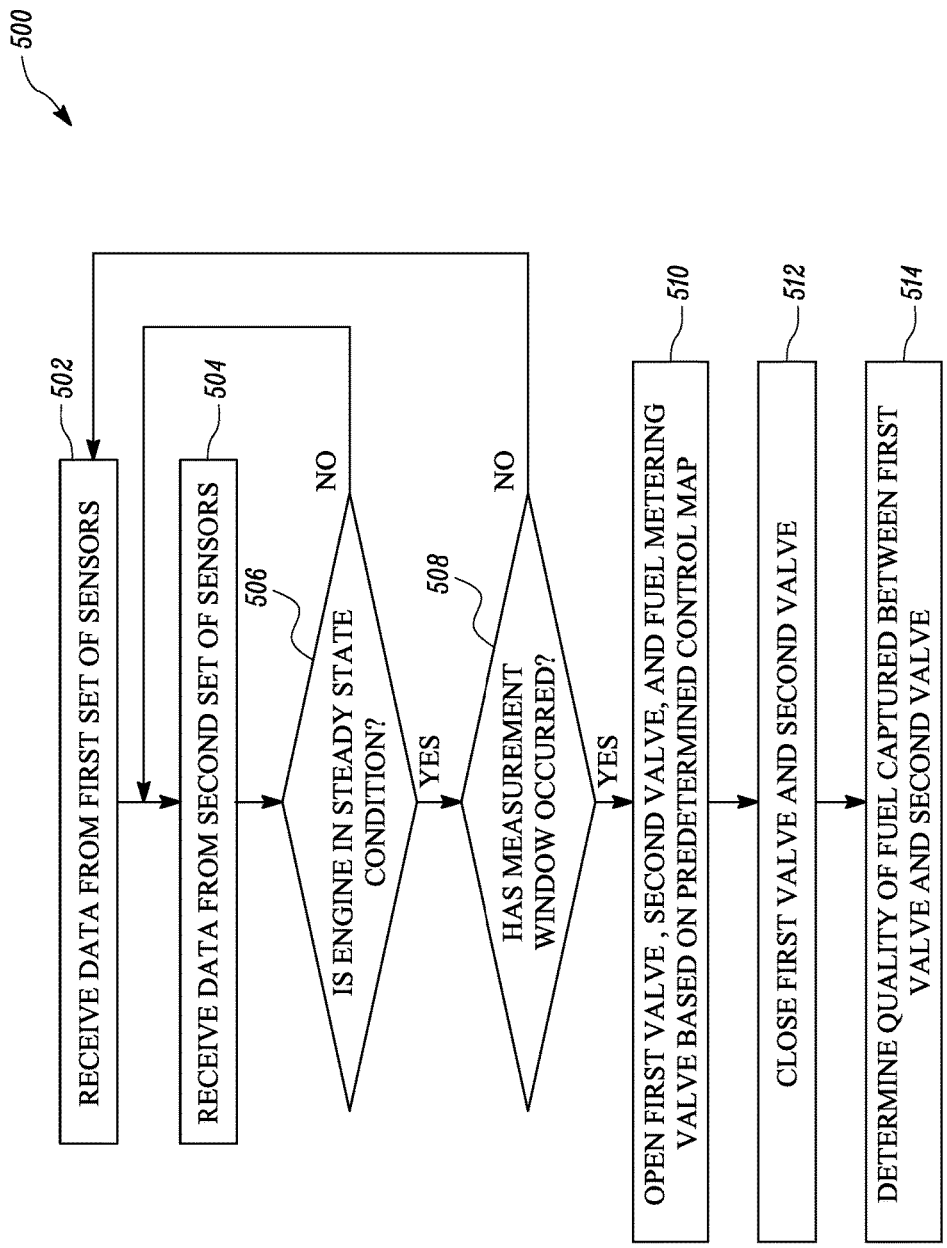
FIG. 5 is a flowchart for a method for determining quality of fuel in the engine, according to one implementation of the present disclosure.

FIG. 5 illustrates a flowchart for the method 500 for determining the quality of the fuel in the engine 100, when the engine 100 is in the normal operation mode, according to some implementations of the present disclosure. For the sake of brevity, some aspects of the present disclosure which are already explained in detail in the description of FIG. 1, FIG. 2, FIG. 3, and FIG. 4 are not explained in the description of FIG. 5.

At block 502, the method 500 may include receiving pressure data from the first set of sensors 202. The pressure data may include, but are not limited to, the pressure "P1" of the fuel at the inlet 206 to the fuel quality measuring unit 128, and/or the "IMP". In some implementations, the data receiving module 312 of the controller 144 of the system 102 may receive the pressure data from the first set of sensors 202.

At block 504, the method 500 may include receiving data from the second set of sensors 204. The data received from the second set of sensors 204 may include, but are not limited to, the at least one value of the one or more engine operating parameters. The one or more engine operating parameters may include, but are not limited to, the engine speed, the engine load, the coolant temperature, the compressor out-pressure, the waste-gate valve position, the throttle valve position, and/or the compressor bypass valve position. In some implementations, the data receiving module 312 of the system 102 may receive the data from the second set of sensors 204.

At block 506, the method 500 may include determining whether the engine 100 is running in the steady state condition. In some implementations, when it may be determined that the engine 100 is not running in the steady state condition, the method 500 may branch back to the block 504. In some implementations, when it may be determined that the engine 100 is running in the steady state condition, the method 500 may branch to a block 508.

At the block 508, the method 500 may include identifying the occurrence of the measurement window. In some implementations, when it may be determined that the measurement window has not occurred, the method 500 may branch back to the block 502. In some implementations, when it may be determined that the measurement window may have occurred, the method 500 may branch to a block 510.

At the block 510, the method 500 may include opening the first valve 130 and the second valve 134 for a predefined time duration, based on the predefined control map. The first valve 130 and the second valve 134 may be opened to allow the fuel to reach the intake manifold 108 through the second flow path "F2". In some implementations, the controlling module 316 of the controller 144 may open the first valve 130 and the second valve 134.

At block 512, the method 500 may include closing the first valve 130 and the second valve 134 once the predefined time duration is completed. The closing of the first valve 130 and the second valve 134 may result into capturing of the fuel between the first valve 130 and the second valve 134. In some implementations, the controlling module 316 of the controller 144 may close the first valve 130 and the second valve 134.

At block 514, the method 500 may include determining the quality of the fuel captured between the first valve 130 and the second valve 134, based on the one or more values detected by the quality measurement sensor 132.

Figure 6:
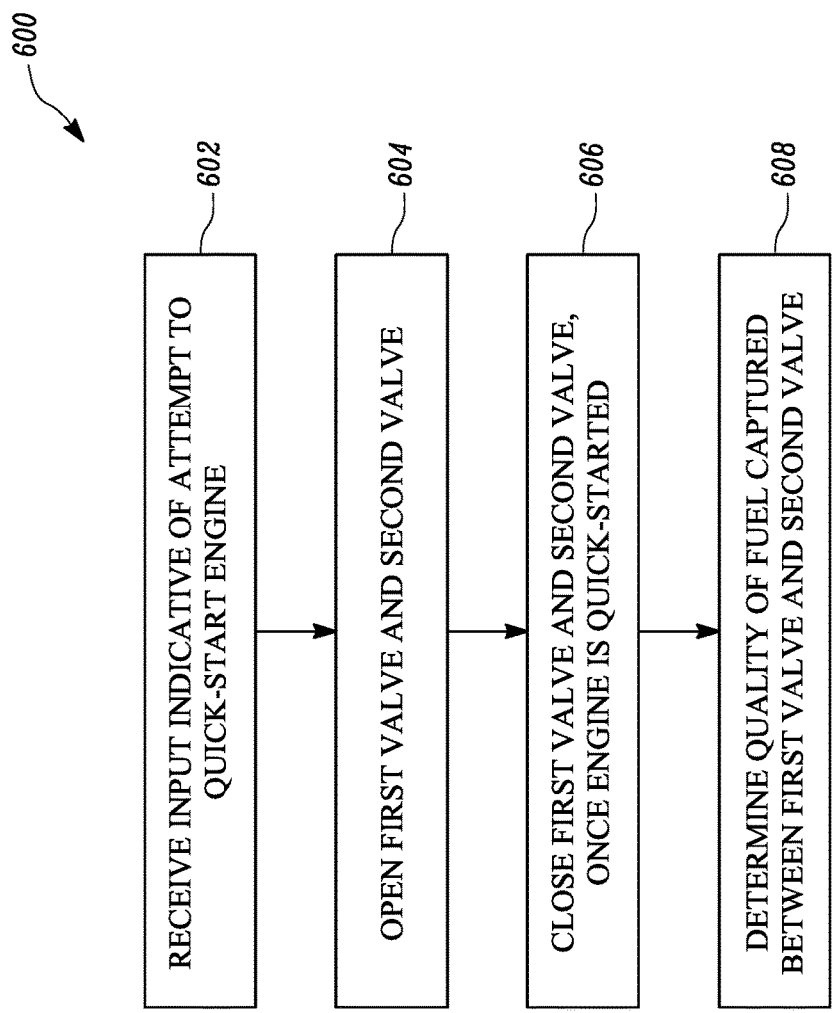
FIG. 6 is a flowchart for a method for determining quality of fuel in the engine, according to one implementation of the present disclosure.

FIG. 6 illustrates a flowchart for the method 600 for determining the quality of the fuel in the engine 100, according to yet another implementation of the present disclosure. The method 600 is for determining the quality of the fuel in the engine 100, when the engine 100 is in the quick-start mode. For the sake of brevity, some aspects of the present disclosure which are already explained in detail in the description of FIG. 1, FIG. 2, FIG. 3, FIG. 4, and FIG. 5 are not explained in the description of FIG. 6.

At block 602, the method 600 may include receiving the input being indicative of the attempt to quick-start the engine 100. The input may be received when the operator may use the input device for giving instructions to quick-start the engine 100. In some implementations, the data receiving module 312 of the controller 144 may receive the input.

At block 604, the method 600 may include opening the first valve 130 and the second valve 134 for receiving the fuel from the fuel admission valve 110, based on the input, for quick-starting the engine 100. In some implementations, the controlling module 316 of the controller 144 may open the first valve 130 and the second valve 134.

At block 606, the method 600 may include closing the first valve 130 and the second valve 134, once the engine 100 may be started. The first valve 130 and the second valve 134 may be closed to capture the fuel between the first valve 130 and the second valve 134. In some implementations, the starting of the engine 100 may be detected based on the at least value of the one or more engine operating parameters detected by the second set of sensors 204. In some implementations, the controlling module 316 of the controller 144 may close the first valve 130 and the second valve 134.

At block 608, the method 600 may include determining the quality of the fuel captured between the first valve 130 and the second valve 134 based on the one or more values detected by the quality measurement sensor 132. In some implementations, the quality determining module 318 of the controller 144 may determine the quality of the fuel.

The system 102 and the methods 400, 500, 600 of the present disclosure offer a comprehensive approach for determining the quality of the fuel in the engine 100. The system 102 may include few components and therefore, can be implemented in the engine 100 without making significant changes in the already existing construction of the engine 100. For example, the quality measurement sensor 132 may be installed between the first valve 130 and the second valve 134, which are being used for quick-starting the engine 100. Therefore, the need to install additional valves and conduits has been eliminated. This in turn would result into a significant reduction in the cost associated with installing, operation, and maintenance of the system 102 for determining the quality of the fuel.

Further, the system 102 and the methods 400, 500, 600 determine the quality of the fuel, when the engine 100 is in different operational modes. For example, the quality of the fuel may be determined when the engine 100 is in the quick-start mode as well as the normal operation mode. Furthermore, since the quality of the fuel is determined during the starting of the engine 100, the engine 100 can be accordingly operated in the normal operation mode in an effective manner. This would negate the possibility of combustion of the fuel with poor quality by detecting such portion of the fuel well in time. In addition, the report indicative of the quality of the fuel may be utilized to improve the operations of the engine 100. As a result, an overall fuel efficiency of the engine 100 may be significantly improved.

Moreover, since the system 102 may control the fuel metering valve 112 of the first flow path "F1" while controlling the first valve 130 and the second valve 134, an overall operation of the engine 100 may not be hampered due to irregularity in fuel delivery to the intake manifold 108. Therefore, the present disclosure offers the system 102 and the methods 400, 500, 600 for determining the quality of the fuel in the engine 100 that are simple, effective, economical, flexible, and time saving.

While aspects of the present disclosure have been particularly shown and described with reference to the implementations above, it will be understood by those skilled in the art that various additional implementations may be contemplated by the modification of the disclosed machines, systems and methods without departing from the spirit and scope of what is disclosed. Such implementations should be understood to fall within the scope of the present disclosure as determined based upon the claims and any equivalents thereof.

What is claimed is:

1. A system for measuring quality of fuel in an engine, the system comprising:
   a fuel quality measuring unit disposed between a fuel admission valve and an intake manifold of the engine, the fuel quality measuring unit comprising a first valve fluidly coupled to the fuel admission valve, a second valve fluidly coupled to the intake manifold, and a quality measurement sensor disposed between the first valve and the second valve; and
   a controller in communication with the fuel quality measuring unit, the controller being configured to:
      determine whether the engine is running in a steady state condition based on one or more engine operating parameters;
      identify a measurement window based on a pressure of the fuel at an inlet to the fuel quality measuring unit, an Intake Manifold Pressure (IMP), and determining whether the engine is running in the steady state condition,
         wherein the measurement window is indicative of a time duration when a value of at least one calibration parameter of the engine is within a predefined range of calibration points for the at least one calibration parameter;
      control, during the measurement window, an opening and a closing of the first valve, the second valve, and a fuel metering valve of the engine during the measurement window, based on a predefined control map,
         the opening and the closing being controlled to capture the fuel between the first valve and the second valve; and
      determine the quality of the fuel captured between the first valve and the second valve based on one or more values detected by the quality measurement sensor.

2. The system of claim 1, wherein:
the first valve is configured to allow a passage of the fuel from the fuel admission valve to the intake manifold through the fuel quality measuring unit;
the quality measurement sensor is disposed downstream with respect to the first valve and is configured to detect the one or more values, the one or more values relating to the quality of the fuel; and
the second valve is disposed downstream with respect to the quality measurement sensor and is configured to allow the fuel to reach the intake manifold.

3. The system of claim 1, further comprising a first set of sensors configured to detect the IMP and the pressure of the fuel at the inlet to the fuel quality measuring unit.

4. The system of claim 3, further comprising a second set of sensors configured to detect at least one value of the one or more engine operating parameters,
wherein the one or more engine operating parameters include at least one of an engine speed, an engine load, a coolant temperature, a compressor out-pressure, a waste-gate valve position, a throttle valve position, or a compressor bypass valve position.

5. The system of claim 4, wherein the steady state condition of the engine indicates that the at least one value of the one or more engine operating parameters is constant over a predetermined time duration.

6. The system of claim 1, wherein the at least one calibration parameter includes at least one of an ignition mode, an ignition timing, or a fuel quantity.

7. The system of claim 1, wherein the controller is configured to determine the quality of the fuel based on at least one of a heat transfer within the fuel or a thermal conductivity of the fuel.

8. The system of claim 1, wherein the pressure of the fuel, at the inlet to the fuel quality measuring unit, is greater than the IMP during the measurement window.

9. A method for determining quality of fuel in an engine, the method comprising:
determining, by a controller, whether the engine is running in a steady state condition based on one or more engine operating parameters;
identifying, by the controller, a measurement window based on a pressure of the fuel at an inlet to a fuel quality measuring unit disposed between a fuel admission valve and an intake manifold of the engine, an Intake Manifold Pressure (IMP), and determining whether the engine is running in the steady state condition, wherein the measurement window is indicative of a time duration when a value of at least one calibration parameter is within a predefined range of calibration points for the at least one calibration parameter;
controlling, by the controller, an opening and a closing of a first valve, a second valve, and a fuel metering valve of the engine during the measurement window, based on a predefined control map, the opening and the closing being controlled to capture the fuel between the first valve and the second valve, wherein the first valve is fluidly coupled to the fuel admission valve and the second valve is fluidly coupled to the intake manifold; and
determining, by the controller, the quality of fuel captured between the first valve and the second valve based on one or more values detected by a quality measurement sensor of the fuel quality measuring unit disposed between the first valve and the second valve.

10. The method of claim 9, further comprising receiving, from a first set of sensors, the IMP and the pressure of the fuel at the inlet to the fuel quality measuring unit.

11. The method of claim 10, further comprising receiving, from a second set of sensors, at least one value of the one or more engine operating parameters,
wherein the one or more engine operating parameters include at least one of an engine speed, an engine load, a coolant temperature, a compressor out-pressure, a waste-gate valve position, a throttle valve position, or a compressor bypass valve position.

12. The method of claim 11, wherein the steady state condition of the engine is indicative of the at least one value of the one or more engine operating parameters being constant over a predetermined time duration.

13. The method of claim 9, further comprising:
receiving an input being indicative of an attempt to quick-start the engine;
opening the first valve and the second valve for receiving the fuel from the fuel admission valve based on the input, for quick-starting the engine;
closing the first valve and the second valve, once the engine is quick-started, for capturing the fuel between the first valve and the second valve; and
determining the quality of the fuel captured between the first valve and the second valve based on the one or more values detected by the quality measurement sensor.

14. The method of claim 9, further comprising controlling the opening and the closing of the first valve and the second valve to create a stationary flow condition of the fuel for detection of the one or more values by the quality measurement sensor.

15. The method of claim 9, wherein the quality of the fuel is determined based on at least one of a heat transfer within the fuel or a thermal conductivity of the fuel.

16. A system for measuring quality of fuel in an engine, the system comprising:
a fuel quality measuring unit disposed between a fuel admission valve and an intake manifold of the engine, the fuel quality measuring unit comprising a first valve fluidly coupled to the fuel admission valve, a second valve fluidly coupled to the intake manifold, and a quality measurement sensor disposed between the first valve and the second valve;
and
a controller in communication with the fuel quality measuring unit, the controller being configured to:
receive an input being indicative of an attempt to quick-start the engine;
open the first valve and the second valve for receiving the fuel from the fuel admission valve based on the input for quick-starting of the engine;
close the first valve and the second valve, once the engine is quick-started, for capturing the fuel between the first valve and the second valve; and
determine the quality of the fuel captured between the first valve and the second valve based on one or more values detected by the quality measurement sensor.

17. The system of claim 16, wherein:
the first valve is configured to allow a passage of the fuel from the fuel admission valve to the intake manifold through the fuel quality measuring unit;
the quality measurement sensor is disposed downstream with respect to the first valve and is configured to detect the one or more values, the one or more values relating to the quality of the fuel; and the second valve is disposed downstream with respect to the quality measurement sensor and is configured to allow the fuel to reach the intake manifold.

18. The system of claim 16, further comprising a second set of sensors configured to detect at least one value of one or more engine operating parameters,
wherein the one or more engine operating parameters include at least one of an engine speed, an engine load, a coolant temperature, a compressor out-pressure, a waste-gate valve position, a throttle valve position, or a compressor bypass valve position.

19. The system of claim 18, wherein a starting of the engine is detected based on the at least one value of the one or more engine operating parameters.

20. The system of claim 16, wherein the controller is configured to determine the quality of the fuel based on at least one of a heat transfer within the fuel or a thermal conductivity of the fuel.

* * * * *